United States Patent [19]

Kato

[11] Patent Number: 4,560,495

[45] Date of Patent: Dec. 24, 1985

[54] DIACYL PEROXIDE COMPOSITION

[75] Inventor: Kenji Kato, Kariya, Japan

[73] Assignee: Nippon Oil and Fats Co., Ltd., Tokyo, Japan

[21] Appl. No.: 636,202

[22] Filed: Jul. 31, 1984

[30] Foreign Application Priority Data

Aug. 5, 1983 [JP] Japan .................................. 58-142593
Oct. 31, 1983 [JP] Japan .................................. 58-202705

[51] Int. Cl.$^4$ .......................... C11D 3/39; C08K 5/14; B01J 31/02
[52] U.S. Cl. ................................ 252/186.23; 502/160; 525/27; 526/232
[58] Field of Search ................... 502/160; 252/186.23, 252/186.26; 568/566, 559; 525/27; 526/232; 156/332

[56] References Cited

U.S. PATENT DOCUMENTS

| | | | |
|---|---|---|---|
| 3,290,257 | 12/1966 | Bader et al. | 502/160 |
| 3,959,241 | 5/1976 | Jaspers | 526/232 |
| 4,151,106 | 4/1979 | Meenem | 502/160 |

*Primary Examiner*—P. E. Konopka
*Attorney, Agent, or Firm*—Flynn, Thiel, Boutell & Tanis

[57] ABSTRACT

A diacyl peroxide composition comprising 10 to 60 parts by weight of peroxide which comprises dibenzoyl peroxide, either di-m-toluoyl peroxide, or di-o-toluoyl peroxide or m-toluoyl o-toluoyl peroxide and either benzoyl m-toluoyl peroxide or benzoyl o-toluoyl peroxide and 90 to 40 parts by weight of a solvent which dissolves the diacyl peroxides does not cause the deposition of the solid matters when kept below 5° C., the phase separation nor the storage degradation for a long term and can be stored for a long time.

The composition usually has peroxide components which are suitable for use in place of benzoyl peroxide and excellent in the handling and the workability.

2 Claims, No Drawings

DIACYL PEROXIDE COMPOSITION

BACKGROUND OF THE INVENTION

Field of the Invention

This invention relates to a diacyl peroxide composition comprising a particular diacyl peroxide mixture which is dissolved in a solvent in a particular ratio, and particularly to a diacyl peroxide composition which is less degradable on storage under cooling to facilitate a long term storage and which is excellent in processability and workability.

Heretofore, dibenzoyl peroxide (hereinafter referred to as BPO), which is a member of the class of diacyl peroxides, has been widely used as a polymerization initiator for vinyl monomers, a curing agent of unsaturated polyester resins and also a cross-linking agent for silicone rubbers and the like.

However, there are drawbacks in that BPO which is in a pure state or a wet state, has little solubility in the monomer, solvent or unsaturated polyester resin, and in addition, a poor dissolving ability due to the solid nature thereof so that it takes a long time to dissolve the same.

Moreover, there is a danger in that pure BPO may sensitively respond to a friction or impact to cause an explosive decomposition.

In order to ameliorate these drawbacks, BPO has been incorporated in various physical forms, for example it is dispersed in a plasticizer which is solid at room temperature, or is dispersed in a liquid plasticizer to give a paste state.

However, there are problems in that the time needed for dissolving it in a monomer or unsaturated polyester resin can be hardly shortened because those of the powder or paste state show a poor workability for measuring the quantity thereof or dissolving them.

There is disclosed in Japanese patent publication NO. 8 905/1965 a liquid curing agent in which a plasticizer is added into di-o-toluoyl peroxide (hereinafter referred to as OTPO) or di-m-toluoyl peroxide (hereinafter referred to as MTPO) for solving this problem.

For this liquid curing agent the dissolving process is not required and the amount measurement as well as the admixing are easily carried out.

This liquid curing agent is also excellent for pump transportation. However, there is still a further problem in this liquid curing agent. It has been known that storage under cooling is usually necessary for peroxides such as BPO in a dissolved state in order to store them without storage degradation for a long term.

Nevertheless, it is preferable to store this liquid curing agent at 14°~30° C. because there is a problem, when it is stored below 5° C., in that a deposition of solid components or a phase-separation occurrs.

SUMMARY OF THE INVENTION

An object of this invention is to provide a diacyl peroxide composition in which deposition of solid components or the phase separation under cooling below 5° C. does not occur.

Another object of this invention is to provide a diacyl peroxide composition which can be stored for a long term without storage degradation.

A further object of this invention is to provide a diacyl peroxide composition which further contains high purity peroxide components suitable for ordinary use.

A still further object of this invention is to provide a diacyl peroxide composition which is especially excellent in easy handling and the workability.

This invention is based on the findings that a composition obtained by dissolving a mixture of a particular content ratio of BPO, a diacyl peroxide such as MTPO and/or OTPO or m-toluoyl o-toluoyl peroxide and a benzoyl m- (and/or o-) toluoyl peroxide having an asymmetrical structure and containing a benzoyl group in the molecule, into a particular amount of a solvent fits the above-mentioned object.

This invention is a diacyl peroxide composition comprising:

(a): 10 to 60 parts by weight of peroxide comprising 1 to 40% by weight of benzoyl peroxide (BPO), 79 to 5% by weight of a peroxide selected from the group consisting of di-m-toluoyl peroxide (referred to as MTPO), di-o-toluoyl peroxide (referred to as OTPO), m-toluoyl o-toluoyl peroxide (referred to as MOTPO) and a mixture thereof and 20 to 55% by weight of peroxide selected from the group consisting of benzoyl m-toluoyl peroxide (referred to as BMTPO), benzoyl-o-toluoyl peroxide (referred to as BOTPO) and a mixture thereof, based on 100% by weight of the sum of BPO,MTPO,OTPO, MOTPO, BMTPO and BOTPO, and (b): 90 to 40 parts by weight of solvent, which dissolves said peroxides of (a).

The respective content ratios of the diacyl peroxides of this invention are those as mentioned above.

However the objects of the diacyl peroxide composition of this invention, namely that it has a practically preferable purity of the diacyl peroxides and can be stored for a long term under cooling without depositing of the solid matters cannot be obtained when BPO exceeds 40% by weight, when MTPO and OTPO or MOTPO exceeds 79% by weight, or when BMTPO or BOTPO is less than 20% by weight.

In addition, the diacyl peroxide compositions having the ratios, in which they have BPO in less than 1% by weight, or BMTPO or BOTPO in more than 55% by weight, are not preferable becase they cannot be produced in ordinary synthetic processes.

The diacyl peroxide composition of this invention comprising 10 to 60 parts by weight of diacyl peroxides which comprises particular content ratios of the above-mentioned components and 90 to 40 parts by weight of a solvent which dissolves the diacyl peroxides.

A composition having less than 10% by weight of diacyl peroxide is not practical because it is excessively dilute, while the content of more than 60% by weight is not preferable because it causes the deposition of solid matters on storage under cooling.

As to the content ratio, the composition comprising 20 to 50 parts by weight of the diacyl peroxide and 80 to 50 parts by weight of the solvent which dissolves the diacyl peroxides is more preferable for its practical use because it is handled easily.

As for the solvent which is used in the composition of this invention, ones which are liquid at ordinary temperature and which are industrially used, for example, aromatic hydrocarbons, halogenated hydrocarbons, ethers, ketones, esters and solvents used in coatings are mentioned.

Examples of the aromatic hydrocarbons are benzene, toluene, xylene, ethylbenzene and the like. Examples of the halogenated hydrocarbons are carbon tetrachloride, chloroform, trichloroethylene and the like.

Examples of the ethers are n-butyl ethyl, isoamyl ether and the like. Examples of the ketones are methyl isobutyl ketone and the like. Examples of esters are dimethylphthalate, di-2-ethylhexyl phthalate, dioctyl phthalate, dioctyl adipate, ethyl propionate, n-butyl adipate, ethyl propionate, n-butyl acetate, ethyl acetate and the like.

As for the solvents used in coating, ethylene glycol diethyl ether, ethyleneglycol monobutyl ether, diethyleneglycol monobutyl ether and the like are exemplified.

One or more than one species of these solvents are mixed and then are used.

It is also possible for the production of the diacylperoxide composition of this invention that after the diacyl peroxide components are synthesized according to known processes, then the resulting respective diacyl peroxide components are mixed to dissolve them in the solvent.

In general, 5 to 60 mol % for preparing benzoyl chloride which is a raw material for preparing the diacyl peroxide, and 95 to 40 mol % of toluoyl chloride are mixed, the resulting mixture is added dropwise into a mixture of the solvent and an aqueous alkaline solution of hydrogen peroxide at a temperature of 10° to 30° C. and then the organic layer separated from the resulting reaction product is washed with water to remove impurities followed by the filtration after it is dehydrated by employing a dehydrating agent to obtain the object composition.

Physical characteristics of the diacyl peroxide components of the composition of this invention are shown in Table 1.

radation with the passing of time, when kept below 5° C. under cooling.

Consequently it can be stored for a long term.

In addition, it has high purity peroxide components which are suitable for ordinary use, and furthermore it is excellent in handling and workability.

The composition of this invention can be employed in the similar manner as BPO in uses where BPO has been heretofore employed.

This invention is further illustrated in the following Examples and Reference Example, Which are, however, not to restrict this invention.

PREFERRED EMBODIMENTS

Example 1

Into a four necked flask of 2 liter capacity, 480 g (1.2 moles) of 10% by weight sodium hydroxide were charged and then 40.8 g (0.6 mole) of 50% aqueous hydrogen peroxide were added under stirring.

Then 200 g of xylene were added and kept at 25° C. Then a liquid mixture of 14.1 g (0.1 mole) of benzoylchloride and 139.1 g (0.9 mole) of m-toluoyl chloride was introduced during 30 minutes, while the content of the flask was cooled in an ice water bath and the resulting mixture was kept at 25° C. After that, the stirring was continued for 1 hour and the resulting mixture was moved into a separation funnel to separate the aqueous phase.

After the organic phase was twice washed with 1 l of water and dehydrated by 20 g of anhydrous magnesium sulfate, it was filtered to give 310.4 g of colorless and clear solution.

TABLE 1

| component | constitutional formula | 10 hours half life periode temperature (°C.) | Amount of theoretical active oxygen (%) |
|---|---|---|---|
| BPO | C₆H₅—C(=O)—OO—C(=O)—C₆H₅ | 74 | 6.61 |
| MTPO | (m-CH₃-C₆H₄)—C(=O)—OO—C(=O)—(m-CH₃-C₆H₄) | 73 | 5.92 |
| OTPO | (o-CH₃-C₆H₄)—C(=O)—OO—C(=O)—(o-CH₃-C₆H₄) | 57 | 5.92 |
| BMTPO | C₆H₅—C(=O)—OO—C(=O)—(m-CH₃-C₆H₄) | 66 | 6.27 |
| MOTPO | (m-CH₃-C₆H₄)—C(=O)—OO—C(=O)—(o-CH₃-C₆H₄) | 65 | 5.92 |

The diacyl peroxide composition of this invention which is constituted as described above, scarcely exhibits deposition of solid matters, phase separation, or degradation The active oxygen content of this solution was assayed by iodometry and the content ratio of the diacyl peroxide components was measured by high performance liquid chromatography.

The content ratio of diacyl peroxides in the composition was also calculated. The obtained results are shown in Table 2.

MTPO. 35 g of this MTPO and 65 g of dimethyl phthalate were admixed to give a homogeneous solution.

As to this solution, the storage stability test was carried out. The result is shown in Table 3.

TABLE 2

| Component | Charging amount of benzoyl chloride (mol) | Charging amount of m-toluoyl chloride (mol) | Solvent | Amount of solvent (mol) | Amount of resultant product (g) | Amount of active oxygen (%) | Component ratios of diacyl peroxide (wt %) BPO:MTPO:BMTPO | Content ratio of diacyl peroxide (wt %) |
|---|---|---|---|---|---|---|---|---|
| Example 1 | 0.1 | 0.9 | Xylene | 200 | 310.4 | 2.33 | 1:79:20 | 38.8 |
| Example 2 | 0.2 | 0.8 | Xylen | 100 | 210.2 | 3.43 | 5:60:35 | 56.6 |
| Example 3 | 0.3 | 0.7 | Xylen | 150 | 266.3 | 2.80 | 10:46:44 | 45.8 |
| Example 4 | 0.4 | 0.6 | Toluene | 200 | 304.7 | 2.43 | 17:34:49 | 39.1 |
| Example 5 | 0.6 | 0.4 | Toluene | 650 | 755.3 | 0.96 | 38:12:50 | 15.1 |
| Example 6 | 0.3 | 0.7 | Ethylen glycol monobutyl ether | 200 | 232.2 | 2.25 | 10:47:43 | 36.7 |
| Example 7 | 0.3 | 0.7 | Dimethyl phthalate | 150 | 221.1 | 3.03 | 8:48:44 | 49.5 |
| Example 8 | 0.3 | 0.7 | Trichloro ethylene | 250 | 280.6 | 1.97 | 11:45:44 | 31.0 |
| Comparative example 1 | 0.7 | 0.3 | Xylene | 730 | 827.0 | 0.85 | 50:7:43 | 13.3 |
| Comparative example 2 | 0.8 | 0.2 | Xylene | 1180 | 1275.0 | 0.56 | 60:5:35 | 8.6 |

Then, the composition was charged in glass vessels and sealed, which vessels were stored in thermostatic chambers kept at −5°, 5° and 15° C. respectively and then the active oxygen content of the composition were determined after 3, 6 and 12 months.

The content ratio of the storage degradation was measured by the decreasing rate of the active oxygen content.

The results are shown in Table 3.

EXAMPLES 2–8

The respective reaction mixtures were obtained according to the same procedures as described in Example 1, except that the molar amount of benzoyl chloride, specie of solvent and amount of the solvent were changed as listed in Table 2.

The active oxygen contents, content ratio of the compositions and the content ratios of diacyl peroxides in the respective compositions were measured by the same methods as those in Example 1.

The obtained results are shown in Table 2.

The storage stability tests were carried out under the same condition as in Example 1.

The obtained results are shown in Table 3.

Comparative Tests 1 and 2

The respective reaction mixtures were obtained according to the same procedures those as described in Example 1 except that the molar amounts of benzoyl chloride and m-toluoyl chloride were changed.

The active oxygen contents, and the component ratios of the obtained compositions and the content ratios of diacyl peroxides in the obtained compositions were measured by the same methods as those in Example 1.

The obtained results are shown in Table 2.

The storage stability tests were carried out under the same conditions as in Example 1.

The obtained results are shown in Table 3.

Comparative Test 3

MTPO was synthesized according to a known process. That is, m-toluoyl chloride was added dropwise into a mixture of sodium hydroxide aqueous solution and aqueous hydrogen peroxide solution to synthesize

TABLE 3

| Composition | Storage Temperature (°C.) | Storage degradation ratio with elapse of time (%) | | |
|---|---|---|---|---|
| | | After 3 months | After 6 months | After 12 months |
| Example 1 | −5 | 0 | 0 | 2 |
| | 5 | 2 | 6 | 12 |
| | 15 | 7 | 23 | 64 |
| Example 2 | −5 | 0 | 0 | 2 |
| | 5 | 2 | 6 | 10 |
| | 15 | 8 | 25 | 60 |
| Example 3 | −5 | 0 | 0 | 2 |
| | 5 | 1 | 8 | 14 |
| | 15 | 7 | 25 | 60 |
| Example 4 | −5 | 0 | 0 | 2 |
| | 5 | 1 | 7 | 16 |
| | 15 | 7 | 28 | 64 |
| Example 5 | −5 | 0 | 0 | 3 |
| | 5 | 1 | 6 | 12 |
| | 15 | 8 | 25 | 62 |
| Example 6 | −5 | 0 | 0 | 4 |
| | 5 | 2 | 8 | 18 |
| | 15 | 10 | 29 | 68 |
| Example 7 | −5 | 0 | 0 | 4 |
| | 5 | 3 | 10 | 22 |
| | 15 | 11 | 28 | 66 |
| Example 8 | −5 | 0 | 0 | 5 |
| | 5 | 3 | 12 | 24 |
| | 15 | 12 | 24 | 72 |
| Comparative Test 1 | −5 | Solid components were deposited | | |
| | 5 | 1 | 8 | 16 |
| | 15 | 8 | 24 | 64 |
| Comparative Test 2 | −5 | Solid components were deposited | | |
| | 5 | 2 | 8 | 17 |
| | 15 | 9 | 26 | 52 |
| Comparative Test 3 | −5 | Solid components were deposited | | |
| | 5 | Solid components were deposited | | |
| | 15 | 12 | 32 | 70 |

Reference Example 1

Thermal curing tests of the respective unsaturated polyester resins were carried out employing the diacylperoxide composition obtained in Example 2 and a paste product comprising 50% by weight of BPO and 50% by weight of dioctylphthalate.

According to JIS-6901 process, a medium reactivity resin of the ortho family was used as the resin and the gelation time, the minimum curing time, the maximum exothermic temperature and Barcoal Hardness were measured at a bath temperature of 80° C.

The obtained results are shown in Table 4.

TABLE 4

| Curing agent | Addition amount of the curing agent (wt % converted value to 100% purity) | Gelation time (min) | Minimum curing time (min) | Maximum exothermic temperature (°C.) | Barcoal Hardness |
|---|---|---|---|---|---|
| Composition of Example 2 | 1 | 4.6 | 6.6 | 212 | 44 |
|  | 0.5 | 10.3 | 14.6 | 188 | 40 |
| BP0 paste | 1 | 4.8 | 6.7 | 208 | 44 |
|  | 0.5 | 10.5 | 14.8 | 197 | 39 |

Example 9

Into a four necked flask of 2 liter capacity, 480 g (1.2 moles) of 10% by weight sodium hydroxide were charged and then 40.8 g (0.6 mole) of 50% aqueous hydrogen peroxide were added under stirring. Then 200 g of xylene was added and kept at 25° C. Then a liquid mixture of 14.1 g (0.1 mole) of benzoyl chloride and 139.1 g (0.9 mole) of o-toluoyl chloride was introduced during 30 minutes, while the content of the flask was cooled in an ice water bath and the resulting mixture was kept at 25° C. After that, the stirring was continued for 1 hour and the resulting mixture was moved into a separation funnel to separate the aqueous phase.

After the organic phase was twice washed with 1 l of water and dehydrated by 20 g of an anhydrous magnesium sulfate and it was filtered to give 302.2 g of colorless and clear solution.

The active oxygen content of this solution was assayed by Iodometry and the content ratio of the diacyl peroxide components was measured by high performance liquid chromatography.

The content ratio of diacyl peroxides in the composition was also calculated. The the obtained results are shown in Table 5.

The results are shown in Table 6.

TABLE 6

| Composition | Storage Temperature (°C.) | Storage degradation ratio with elapse of time(%) | | |
|---|---|---|---|---|
| | | After 3 months | After 6 months | After 12 months |
| Example 9 | −5 | 0 | 0 | 2 |
|  | 5 | 2 | 7 | 11 |
|  | 15 | 8 | 25 | 66 |
| Example 10 | −5 | 0 | 0 | 2 |
|  | 5 | 2 | 6 | 12 |
|  | 15 | 7 | 27 | 64 |
| Example 11 | −5 | 0 | 0 | 1 |
|  | 5 | 2 | 10 | 13 |
|  | 15 | 8 | 27 | 62 |
| Example 12 | −5 | 0 | 0 | 4 |
|  | 5 | 1 | 8 | 16 |
|  | 15 | 8 | 30 | 66 |
| Example 13 | −5 | 0 | 0 | 4 |
|  | 5 | 2 | 8 | 16 |
|  | 15 | 9 | 26 | 68 |
| Example 14 | −5 | 0 | 1 | 3 |
|  | 5 | 2 | 8 | 20 |
|  | 15 | 10 | 28 | 70 |
| Example 15 | −5 | 0 | 0 | 3 |
|  | 5 | 2 | 9 | 22 |
|  | 15 | 11 | 28 | 70 |
| Example 16 | −5 | 0 | 0 | 4 |
|  | 5 | 3 | 11 | 26 |
|  | 15 | 12 | 28 | 78 |
| Comparative Test 4 | −5 | Solid components were deposited | | |
|  | 5 | 1 | 8 | 17 |
|  | 15 | 9 | 26 | 70 |

TABLE 5

| Component | Charging amount of benzyl chloride (mol) | Charging amount of o-toluyl chloride (mol) | solvent | Amount of solvent (mol) | Amount of resultant product (g) | Amount of active oxygen (%) | Component ratios of diacyl peroxide (wt %) BPO:OTPO:BOTPO | Content ratio of deacyl peroxide (wt %) |
|---|---|---|---|---|---|---|---|---|
| Example 9 | 0.1 | 0.9 | Xylene | 200 | 302.2 | 2.30 | 1:74:25 | 38.3 |
| Example 10 | 0.2 | 0.8 | Xylen | 100 | 207.0 | 3.38 | 5:56:39 | 55.6 |
| Example 11 | 0.3 | 0.7 | Xylen | 150 | 260.3 | 2.77 | 10:43:47 | 45.1 |
| Example 12 | 0.4 | 0.6 | Toluene | 200 | 300.3 | 2.41 | 17:31:52 | 38.8 |
| Example 13 | 0.6 | 0.4 | Toluene | 700 | 802.2 | 0.82 | 39:10:51 | 13.0 |
| Example 14 | 0.3 | 0.7 | Dibutyl-phthalate | 150 | 247.6 | 2.76 | 10:41:49 | 44.8 |
| Example 15 | 0.3 | 0.7 | Ethylen glycol monobutyl ether | 250 | 338.0 | 1.96 | 10:42:48 | 32.0 |
| Example 16 | 0.3 | 0.7 | Trichloro ethylene | 250 | 335.2 | 1.96 | 9:40:51 | 31.8 |
| Comparative example 4 | 0.7 | 0.3 | Xylene | 730 | 821.6 | 0.83 | 50:6:44 | 12.9 |
| Comparative example 5 | 0.8 | 0.2 | Xylene | 1180 | 1270.0 | 0.54 | 61:4:35 | 8.4 |

Then, the obtained composition was charged in glass vessels and sealed, which were stored in thermostatic chambers kept at −5°, 5° and 15° C. respectively and then the active oxygen content of the compositions were determined after 3, 6 and 12 months.

The content ratio of the storage degradation was measured by the decreasing rate of the actual oxygen content.

| Comparative Test 5 | −5 | Solid components were deposited | | |
|---|---|---|---|---|
|  | 5 | 2 | 8 | 19 |
|  | 15 | 9 | 32 | 72 |
| Comparative Test 6 | −5 | Solid components were deposited | | |
|  | 5 | Solid components were deposited | | |
|  | 15 | 13 | 35 | 78 |

Examples 10-16

The respective reaction mixtures were obtained according to the same procedures as described in Example 9, except that molar amount of benzoyl chloride, specie of solvent and amount of the solvent were changed.

The active oxygen contents and compositions and the content ratios of diacyl peroxides in the respective obtained compositions were measured by the same methods as those in Example 9.

The obtained results are shown in Table 5.

The storage stability tests were carried out under the same condition as in Example 9.

The obtained results are shown in Table 6.

Comparative Tests 4 and 5

The respective reaction mixtures were obtained according to the same procedures those as described in Example 9 except that the molar amounts of benzoyl chloride and m-toluoyl chloride were changed.

The active oxygen contents, the component ratios of the compositions and the content ratios of diacyl peroxides in the compositions were measured by the same method as those in Example 9.

The obtained results are shown in Table 5.

The storage stability tests were carried out under the same conditions as in Example 9.

The obtained results are shown in Table 6.

Comparative Test 6

OTPO was synthesized according to a known process. This is, o-toluoyl chloride was added dropwise into a mixture of sodium hydroxide aqueous solution and hydrogen peroxide aqueous solution to synthesize OTPO. 35 g of this OTPO and 65 g of dimethyl phthalate were admixed to give a homogeneous solution.

As to this solution, the storage stability test was carried out. The result is shown in Table 6.

Reference Example 2

Thermal curing tests of the respective unsaturated polyester resins were carried out employing the diacylperoxide composition obtained in Example 10 and a paste product comprising 50% by weight of BPO and 50% by weight of dioctylphthalate.

According to JIS-6901 process, a medium reactivity resin of the ortho family was used as the resin and the gelation time, the minimum curing time, the maximum exothermic temperature and Barcoal Hardness were measured at a bath temperature of 80° C.

The obtained results are shown in Tables 7 and 8.

TABLE 7

| Curing agent | Addition amount of the curing agent (wt % converted value to 100% purity) | Gelation time (min) | Minimum curing time (min) | Maximum exothermic temperature (°C.) | Barcoal Hardness |
|---|---|---|---|---|---|
| Composition of Example 10 | 1 | 0.3 | 1.0 | 206 | 46 |
| | 0.5 | 1.7 | 2.3 | 203 | 44 |
| BPO paste | 1 | 4.8 | 6.7 | 208 | 44 |
| | 0.5 | 10.5 | 14.8 | 197 | 39 |

TABLE 8

| Curing agent | Addition amount of the curing agent (wt % converted value to 100% purity) | Addition amount of dimethyl aniline (wt %) | Gelation time (min) | Minimum curing time (min) | Maximum exothermic temperature (°C.) | Barcoal Hardness |
|---|---|---|---|---|---|---|
| Composition of Example 10 | 1 | 0.2 | 4.0 | 6.3 | 134 | 46 |
| | — | 0.1 | 11.6 | 15.5 | 133 | 45 |
| BPO paste | 1 | 0.2 | 12.6 | 17.5 | 130 | 44 |
| | — | 0.1 | 25.5 | 33.7 | 133 | 46 |

Example 17

Into a four necked flask of 2 liter capacity, 480 g (1.2 moles) of 10% by weight sodium hydroxide were charged and then 40.8 g (0.6 mole) of 50% aqueous hydrogen peroxide were added under stirring.

Then, 200 g of xylene were added and kept at 25° C. Then a resultant mixture of 28.2 g (0.2 mole) of benzoyl chloride, 61.8 (0.4 mole) of o-toluoyl chloride and 61.8 g (0.4 mol) of m-toluoyl chloride were incorporated during 30 minutes, while the content of the flask was cooled in an ice water bath and the resulting mixture was kept at 25° C.

After that, the stirring was continued for 1 hour and the resulting mixture was moved into a separation funnel to separate the aqueous phase.

After the organic phase was twice washed with 1 l of water and dehydrated by 20 g of an anhydrous magnesium sulfate and it was filtered to give 303.3 g of colorless and clear solution.

The active oxygen content of this solution was assayed by iodometry and the ratio of the diacyl peroxide component was obtained by the high performance liquid chromatography.

The content ratio of diacyl peroxides in the composition was also calculated.

The obtained results are shown in Table 8.

Then, the composition was charged in glass vessels and sealed, which were stored in thermostatic chambers kept at −5°, 5° and 15° C. respectively and then the active oxygen content of the composition were determined after 3, 6 and 12 months.

The storage degradation ratio of the composition with the passing of time were measured from the decreased amount of the active oxygen.

The obtained results are shown in Table 8.

TABLE 9

| Composition | Charging amount of benzoyl chloride (mole) | Charging amount of m-toluoyl chloride and o-toluoylchloride (mole) | Solvent | Amount of solvent (g) | Amount of obtained composition (g) |
| --- | --- | --- | --- | --- | --- |
| Example 17 | 0.2 | m-0.4<br>o-0.4 | Xylene | 200 | 303.8 |

| Composition | Amount of active oxygen (%) | Content ratio of diacyl peroxide (wt %)<br>BPO MTPO OTPO MOTPO BMTPO BOTPO | Content ratio of diacyl peroxide (wt %) |
| --- | --- | --- | --- |
| Example 17 | 2.26 | 4:16:15:32:17:16 | 37.5 |

TABLE 10

| Composition | Storage Temperature (°C.) | Degradation ratio with elapse of time (%) | | |
| --- | --- | --- | --- | --- |
| | | After 3 months | After 6 months | After 12 months |
| Example 17 | −5 | 0 | 0 | 2 |
| | 5 | 2 | 8 | 11 |
| | 15 | 9 | 22 | 68 |

What is claimed is:

1. A liquid, diacyl peroxide composition, which comprises
   (a) from 10 to 60 parts by weight of diacyl peroxide component, said diacyl peroxide component comprising
      (i) from 1 to 40% by weight of benzoyl peroxide (BPO),
      (ii) from 5 to 79% by weight of a second peroxide selected from the group consisting of di-o-toluoyl peroxide (OTPO), di-m-toluoyl peroxide (MTPO), m-toluoyl-o-toluoyl peroxide (MOTPO) and a mixture thereof; and
      (iii) from 20 to 55% by weight of a third peroxide selected from the group consisting of benzoyl-m-toluoyl peroxide (BMTPO), benzoyl-o-toluoyl peroxide (BOTPO) and a mixture thereof wherein the foregoing percentages are based on 100% by weight of the sum of BPO, MTPO, OTPO, MOTPO, BMTPO, and BOTPO, and
   (b) from 40 to 90 parts by weight of solvent in which said peroxides of (a) are dissolved, so that said liquid diacyl peroxide composition can be stored at a temperature below 5° C. without depositing solids or undergoing phase separation, wherein said solvent is one or more selected from the group consisting of aromatic hydrocarbons, halogenated hydrocarbons, ethers, ketones and esters.

2. A diacyl peroxide composition as claimed in claim 1 in which said composition consists essentially of from 20 to 50 parts by weight of (a) and from 50 to 80 parts by weight of (b).

* * * * *